United States Patent
Datta et al.

(10) Patent No.: US 9,566,158 B2
(45) Date of Patent: *Feb. 14, 2017

(54) HARDWARE PROTECTION OF VIRTUAL MACHINE MONITOR RUNTIME INTEGRITY WATCHER

(75) Inventors: Shamanna M. Datta, Hillsboro, OR (US); Albert J. Munoz, Los Altos, CA (US); Mahesh S. Natu, Sunnyvale, CA (US); Scott T. Durrant, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 180 days.

This patent is subject to a terminal disclaimer.

(21) Appl. No.: 13/995,742

(22) PCT Filed: Dec. 31, 2011

(86) PCT No.: PCT/US2011/068283
§ 371 (c)(1),
(2), (4) Date: Jun. 19, 2013

(87) PCT Pub. No.: WO2013/101248
PCT Pub. Date: Jul. 4, 2013

(65) Prior Publication Data
US 2013/0275980 A1    Oct. 17, 2013

(51) Int. Cl.
*G06F 9/455*    (2006.01)
*A61F 2/34*    (2006.01)
(Continued)

(52) U.S. Cl.
CPC ............ *A61F 2/34* (2013.01); *A61B 17/8066* (2013.01); *A61F 2/30734* (2013.01); *A61F 2/30771* (2013.01); *G06F 9/45533* (2013.01); *A61B 17/82* (2013.01); *A61B 17/866* (2013.01); *A61B 17/8685* (2013.01); *A61F 2/30749* (2013.01); *A61F 2/30907* (2013.01);
(Continued)

(58) Field of Classification Search
None
See application file for complete search history.

(56) References Cited

U.S. PATENT DOCUMENTS 7,707,411 B2 *    4/2010    Bade et al. .................... 713/164
7,962,738 B2 *    6/2011    Zimmer et al. ................... 713/2
(Continued)

OTHER PUBLICATIONS

PCT International Search Report for PCT Counterpart Application No. PCT/US2011/068283, 3 pgs., (Sep. 25, 2012).
(Continued)

*Primary Examiner* — Van Nguyen
(74) *Attorney, Agent, or Firm* — Nicholson De Vos Webster & Elliott LLP

(57) ABSTRACT

An apparatus and method for hardware protection of a virtual machine monitor (VMM) runtime integrity watcher is described. A set of one or more hardware range registers that protect a contiguous memory space that is to store the VMM runtime integrity watcher. The set of hardware range registers are to protect the VMM runtime integrity watcher from being modified when loaded into the contiguous memory space. The VMM runtime integrity watcher, when executed, performs an integrity check on a VMM during runtime of the VMM.

18 Claims, 9 Drawing Sheets

(51) Int. Cl.
*A61B 17/80* (2006.01)
*A61F 2/30* (2006.01)
*A61B 17/82* (2006.01)
*A61B 17/86* (2006.01)
*A61F 2/46* (2006.01)

(52) U.S. Cl.
CPC . *A61F 2/30965* (2013.01); *A61F 2002/30011* (2013.01); *A61F 2002/3038* (2013.01); *A61F 2002/3082* (2013.01); *A61F 2002/3092* (2013.01); *A61F 2002/3096* (2013.01); *A61F 2002/30169* (2013.01); *A61F 2002/30189* (2013.01); *A61F 2002/30326* (2013.01); *A61F 2002/30387* (2013.01); *A61F 2002/30449* (2013.01); *A61F 2002/30462* (2013.01); *A61F 2002/30471* (2013.01); *A61F 2002/30474* (2013.01); *A61F 2002/30507* (2013.01); *A61F 2002/30538* (2013.01); *A61F 2002/30578* (2013.01); *A61F 2002/30579* (2013.01); *A61F 2002/30611* (2013.01); *A61F 2002/30617* (2013.01); *A61F 2002/30736* (2013.01); *A61F 2002/30841* (2013.01); *A61F 2002/348* (2013.01); *A61F 2002/3412* (2013.01); *A61F 2002/3429* (2013.01); *A61F 2002/3441* (2013.01); *A61F 2002/3448* (2013.01); *A61F 2002/3487* (2013.01); *A61F 2002/4615* (2013.01); *A61F 2002/4619* (2013.01)

(56) References Cited

U.S. PATENT DOCUMENTS

| | | | | |
|---|---|---|---|---|
| 8,086,852 B2 * | 12/2011 | Bade et al. | | 713/164 |
| 8,464,251 B2 * | 6/2013 | Sahita et al. | | 718/1 |
| 8,516,481 B2 | 8/2013 | Broyles et al. | | |
| 8,683,548 B1 * | 3/2014 | Curry et al. | | 726/1 |
| 8,701,187 B2 | 4/2014 | Schluessler et al. | | |
| 8,806,486 B2 * | 8/2014 | Martin et al. | | 718/1 |
| 2009/0164770 A1 * | 6/2009 | Zimmer et al. | | 713/2 |
| 2011/0145598 A1 * | 6/2011 | Smith et al. | | 713/190 |
| 2012/0297057 A1 * | 11/2012 | Ghosh et al. | | 709/224 |

OTHER PUBLICATIONS

PCT Written Opinion of the International Searching Authority for PCT Counterpart Application No. PCT/US2011/068283, 3 pgs., (Sep. 25, 2012).

PCT Notification concerning Transmittal of International Preliminary Report on Patentability (Chapter I of the Patent Cooperation Treaty) for PCT Counterpart Application No. PCT/US2011/068283, 5 pgs., (Jul. 10, 2014).

Notice of Allowance from Taiwan Patent Application No. 101148749, mailed Aug. 5, 2014, 3 pages.

* cited by examiner

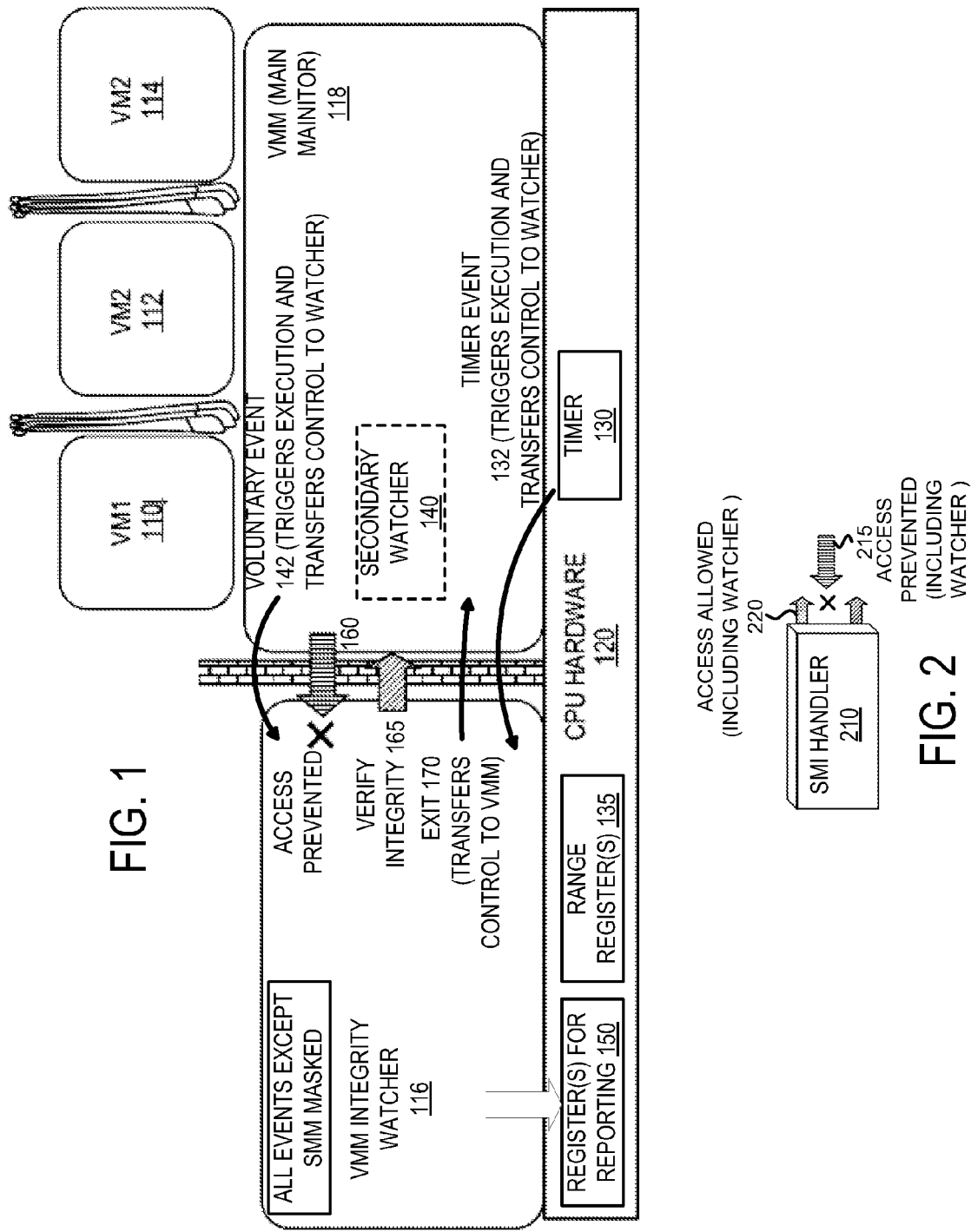

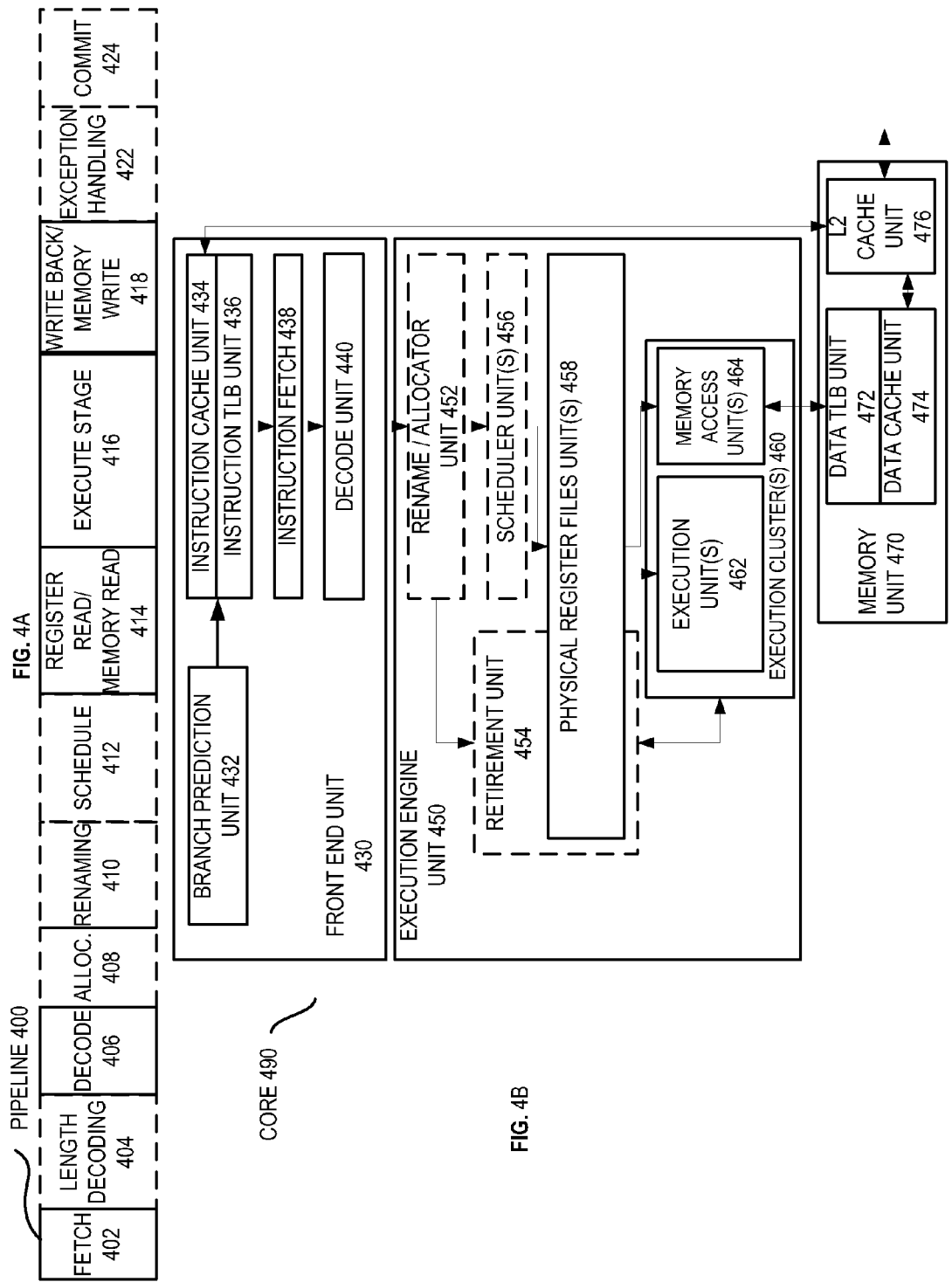

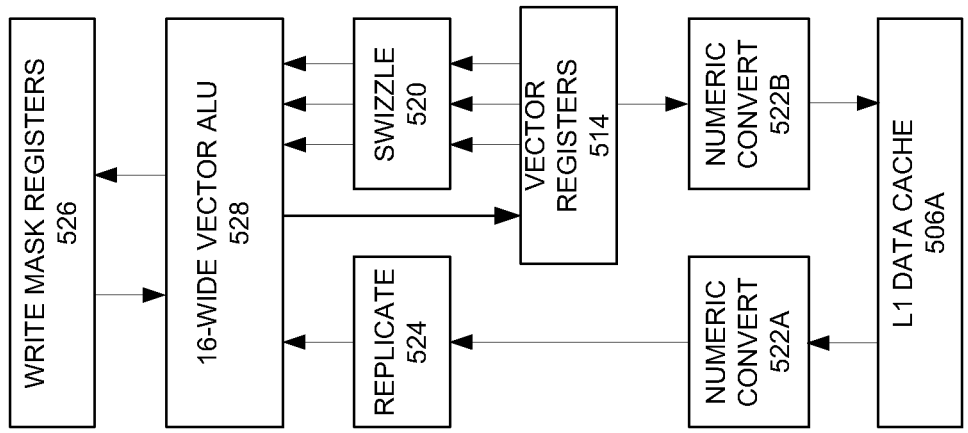
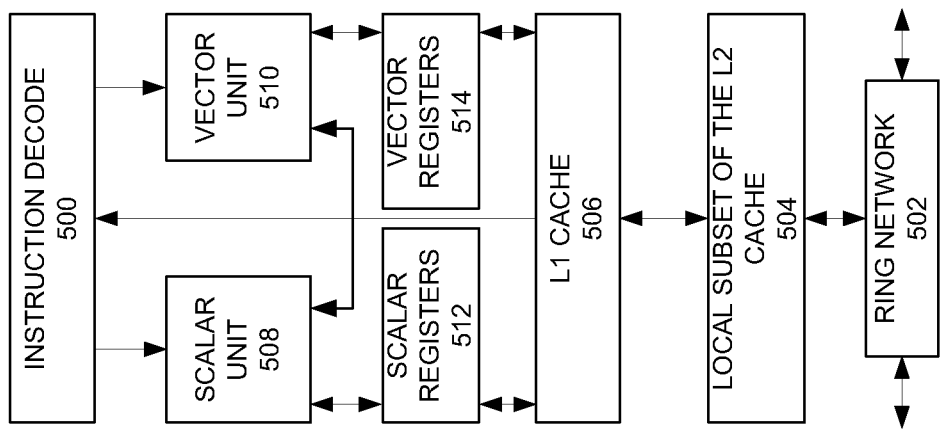

HARDWARE PROTECTION OF VIRTUAL MACHINE MONITOR RUNTIME INTEGRITY WATCHER

CROSS-REFERENCE TO RELATED APPLICATION

This patent application is a U.S. National Phase Application under 35 U.S.C. §371 of International Application No. PCT/US2011/068283, filed Dec. 31, 2011, entitled HARDWARE PROTECTION OF VIRTUAL MACHINE MONITOR RUNTIME INTEGRITY WATCHER.

FIELD

This field of invention relates generally to computer processor architecture, and more specifically, to hardware protection of a virtual machine monitor runtime integrity watcher software.

BACKGROUND

Consumers (and potential consumers) of cloud computing services have expressed reluctance to deploy sensitive data and workloads into cloud infrastructures due to concern about the infrastructure's ability to protect their sensitive information. In a cloud environment, this means providing adequate security for the virtualized environment.

For example, in a virtual environment (as most infrastructure as a service (IaaS) deployments are), it is the job of the virtual machine monitor (VMM) to provide security services to the virtual machines (VMs) it is managing. Accordingly, the VMM has a very high asset value since if it is compromised, then security of all the VMs (workloads) that it is monitoring is also compromised.

Technology exists, such as the Intel Trusted eXecution Technology (TXT) that ensures launch time integrity of a VMM. However, there is currently no technology that ensures VMM integrity during runtime. In a typical virtual IaaS environment, launched VMMs may keep running for over a month at a time thereby increasing the vulnerability of this critical asset (VMM).

BRIEF DESCRIPTION OF THE DRAWINGS

The present invention is illustrated by way of example and not limitation in the figures of the accompanying drawings, in which like references indicate similar elements and in which:

FIG. 1 illustrates an exemplary system for hardware protection of a virtual machine monitor runtime integrity watcher according to one embodiment;

FIG. 2 illustrates that an exemplary SMI handler 210 can access the code space of the watcher of FIG. 1 and accesses from the watcher of FIG. 1 to the code space of the SMI handler are prevented;

FIG. 4A is a block diagram illustrating both an exemplary in-order pipeline and an exemplary register renaming, out-of-order issue/execution pipeline according to embodiments of the invention;

FIG. 4B is a block diagram illustrating both an exemplary embodiment of an in-order architecture core and an exemplary register renaming, out-of-order issue/execution architecture core to be included in a processor according to embodiments of the invention;

FIG. 5A is a block diagram of a single processor core, along with its connection to the on-die interconnect network and with its local subset of the Level 2 (L2) cache, according to embodiments of the invention;

FIG. 5B is an expanded view of part of the processor core in FIG. 5A according to embodiments of the invention;

DETAILED DESCRIPTION

Figure 3:
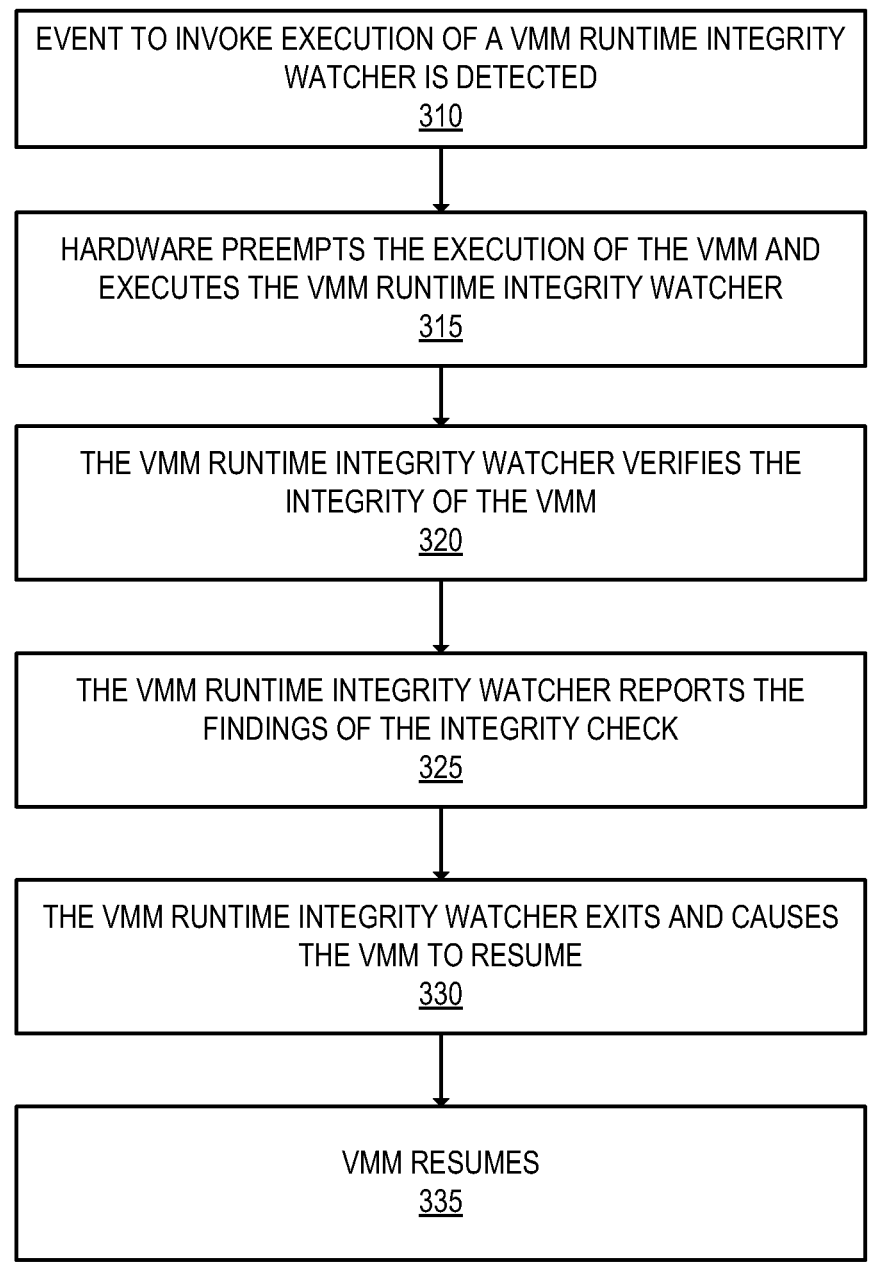
FIG. 3 is a flow diagram illustrating exemplary operations performed by a system providing hardware protection of a VMM runtime integrity checking application according to one embodiment.

In the following description, numerous specific details are set forth. However, it is understood that embodiments of the invention may be practiced without these specific details. In other instances, well-known circuits, structures and techniques have not been shown in detail in order not to obscure the understanding of this description.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As detailed earlier, if a virtual machine monitor (VMM) is compromised, then security of all VMs (workloads) that the VMM is managing is also compromised. Embodiments described herein provide runtime integrity protection for the root VMM.

FIG. 1 illustrates an exemplary system for hardware protection of a virtual machine monitor runtime integrity watcher according to one embodiment. The CPU hardware 120 includes the hardware necessary to execute the virtual machines (VMs) 110-114, the main VMM 118 and the main VMM runtime integrity watcher program 116 ("watcher"). The VMM 118 is the stand alone root VMM that runs on the bear metal and provides security services to the VMs 110-114 and is able to retain selective control of processor resources, physical memory, interrupt management, and data I/O provided through the CPU hardware 120 for the VMs 110-114.

The watcher 116 is a program that monitors the content and behavior of the main VMM 118 (e.g., to detect malware in the VMM 118 or other malicious software or behavior caused by such malware). In one embodiment, the watcher 116 is loaded into a hardware range register protected contiguous memory space from which it has visibility into the entire VMM's memory and resources. Thus, the watcher 116 may monitor the VMM's memory and resources. In one embodiment, hardware range register(s) 135 are defined that define the bounds of the memory address space where the code for the watcher 116 resides.

The hardware range register(s) 135 may be part of the processor core page management unit and work in conjunction with the memory management architecture of the processor. In one embodiment, the VMM 118 sets the values of the hardware range register(s) 135 when it launches and sets a lock bit, which prevents the values to be subsequently changed (unless a reboot occurs).

The hardware range register protected contiguous memory space prevents other entities on the platform, including the VMM 118, from modifying the watcher 116 or affecting its behavior. For example, the CPU hardware 120 sets an internal identifier inside the page management hardware as soon as the code transitions into the hardware range register protected contiguous memory space that are defined by the range registers (e.g., the execution of the watcher 116). This identifier indicates being in watcher mode. As will be described in greater detail later herein, execution of the watcher 116 will be triggered as a result of certain events occurring. Thus, the identifier is set only when the processor execution transfers control to the watcher 116. The identifier is reset when the processor execution transfers control back to the VMM 118.

For example, memory accesses made from the watcher 116 to any other memory space (excluding System Management Code space) is allowed by the page management hardware. For example, the page management unit consults the internal identifier to determine whether memory access is allowed. Access from code that is not executing in the space defined by the hardware range register(s) 135 into the space defined by the range register(s) 135 is directed into an abort page by the page management hardware unit. In such a case, for example, the code executing outside the space defined by the hardware range register(s) 135 will read all ones (0xff). By way of example, as indicated by the block arrow 160, the VMM 118 is prevented from accessing the VMM integrity watcher 116 (e.g., prevented by the page management hardware unit). For example, if the identifier is not set, then the page management unit directs the request to an abort page. The VMM 118 should not be able to make a memory access when the identifier is set, since execution of the VMM 118 is preempted when the event is detected and control moves to the watcher 116.

In one embodiment, access to the memory space defined by the range register(s) 135 from code executing in System Management Mode 135 is allowed. Thus, System Management Mode is treated as a supervisory mode and is allowed to access the watcher 116. The code executing in System Management Mode may be inside a Trusted Computing Base. System Management Mode may allow supervisory functions such as Reliability, Availability, and Serviceability (RAS) to be performed. For example, FIG. 2 illustrates an exemplary SMI handler 210 (which may be inside a Trusted Computing Base) that is able to access 220 the code space of the watcher 116 (e.g., in order to perform RAS functions), and accesses 215 to the code space of the SMI handler 210 from the watcher 116 are prevented.

In one embodiment, the watcher 116 is executed due to a hardware guaranteed immutable triggering mechanism that invokes the execution of the watcher 116. For example, in one embodiment, a hardware timer 130 (which may be randomized) is used to generate an event 132 that causes the execution of the VMM 118 to be preempted and control brought into the watcher 116 (which is loaded in the protected memory space). For example, the hardware timer 130 may initially be programmed with an upper bound value and a lower bound value to generate the timer event 132 at a value randomized between these two values. The advantage of using an upper and lower bound value in the timer 130 and having the timer 130 generate the timer event 132 at a value randomized between these bounds by hardware is that malware that may enter cannot easily guess when the watcher will be invoked. This makes it harder for malware to hide from the watcher 116. This raises the bar against malware that would estimate when the watcher 116 becomes active and try to hide during those times. In other embodiments, the watcher 116 is invoked due to certain events (referred herein as "voluntary events") such as a bad I/O port and control register or machine specific register (MSR) execution, indicated by the voluntary event 142, and control is brought to the watcher 116.

After the execution of the watcher 116 is invoked, it operates in the hardware protected region unaffected by malware and cryptographically verifies the integrity of the VMM 165. In one embodiment, the watcher 116 uses well known cryptographic algorithms (e.g., SHA-2) to compute hash(es) of portions of code and/or data during the first invocation (e.g., when the machine initially boots and performs the first invocation) and storing it in the hardware range register protected memory space. Then, upon subsequent invocations of the watcher 116 during the runtime of the VMM 118, the watcher 116 repeats the hashing operation on those portions of code and/or data to determine whether the hash values are the same. If they are the same, then integrity of the VMM 118 is not compromised. If they are different, then the integrity of the VMM 118 is compromised. In another embodiment, the hash value(s) of the VMM 118 is generated differently, for example during compilation (in such a case it may be signed).

In one embodiment, a secondary watcher program 140 is included within the VMM 118. The secondary watcher program 140 may be scattered throughout memory. The secondary watcher program 140 can run in VMM context. In addition, the secondary watcher program 140 can run with interrupts on. In embodiments where a secondary watcher program 140 is included within the VMM 118, the watcher program 116 verifies the integrity of the secondary watcher program 140 and then transfers responsibility of verifying the integrity of the VMM 118 either partially or fully to the secondary watcher.

In one embodiment, a set of hardware register(s) 130 of the CPU hardware 120 are used for a secure reporting mechanism to report findings of the watcher 116. In one embodiment, the set of hardware register(s) 130 can be only written by the watcher 116, but can be read by any other software entity. For example, a set of one or more uncore registers may be used for reporting. The set of uncore registers may be writable only by the watcher 116 but able to be read by any other software entity. For example, the set of uncore registers may only be written when in the watcher mode, as identified by the identifier previously described. Thus, if not in watcher mode, a write will not be allowed. When in watcher mode, only the watcher should be executing (since the VMM is preempted) and is allowed to write to the set of uncore registers.

In another embodiment, the CPU hardware 120 may provide a secure pathway through other microcontroller(s) that are embedded inside the processor and/or chipset in order to export the report to a management entity (in addition to or in lieu of using the set of hardware register(s)

130 for reporting). Such a management entity may include, for example, a system management application or a cloud management application.

After reporting the results of the integrity check, execution of the watcher 116 exits 170 and control is transferred back to the VMM 118 to resume its execution. By way of example, the watcher 116 issues an instruction architecture trigger (e.g., VMRESUME) instruction causing the VMM 118 to resume its execution.

FIG. 3 is a flow diagram illustrating exemplary operations performed by a system providing hardware protection of a VMM runtime integrity checking application according to one embodiment. FIG. 3 will be described with reference to the exemplary embodiment of FIG. 1. However, it should be understood that the operations described with reference to FIG. 3 can be performed by embodiments different than that described with reference to FIG. 1, and the embodiment described with respect to FIG. 1 can perform operations that are different than that are described with respect to FIG. 3.

At operation 310, an event that will trigger the execution of the watcher 116 is experienced. For example, the event may be a timer event 132 generated by the hardware timer 130. As another example, the event may be a voluntary event 142 such as a bad I/O port or a control register or SMR execution by malware. Flow moves from operation 310 to operation 315.

At operation 315, the event causes the hardware 120 to preempt the execution of the VM 118 and executes the watcher 116. For example, upon the event occurring, the chipset asserts a signal to cause the processor to enter watcher mode at the next instruction boundary. As previously described, in one embodiment the watcher 116 is loaded in a region of contiguous memory space that is protected via hardware range registers from being modified or its behavior affected (including by the VMM 118).

Flow then moves to operation 320, where the watcher 116 verifies the integrity of the VMM. For example, this may include the watcher 116 analyzing the cause of entry (e.g., the reason that it was executed) and generating cryptographic hash(es) of portions of code and/or data of the VMM 118 and comparing it to previously stored values.

In an embodiment where there is a single watcher (that is, in an embodiment where there is not a secondary watcher 140), the watcher 116 performs all analysis and may spend no more than 200 microseconds analyzing the cause of entry since interrupts are off.

In an embodiment where there is a secondary watcher 140 in addition to the watcher 116, the watcher 116 verifies the secondary watcher 140, which runs in VMM context. The secondary watcher 140 can run with the interrupts on. The secondary watcher 140 may either full, or partially, perform the responsibility of VMM malware checking.

Flow moves from operation 320 to operation 325. At operation 325, the watcher 116 reports its findings. For example, the watcher 116 writes to the register(s) 150 to indicate whether the integrity of the VMM 118 has been compromised. As another example, the watcher 116 may, in addition to or in lieu of writing to the register(s) 150, reports the findings (e.g., the status of the integrity of the VMM 118) to a management entity such as a system management application or a cloud management application. In such a case, the CPU hardware 120 may provide a secure pathway through microcontroller(s) that are imbedded inside the processor and/or the chipset.

In an embodiment where there is a secondary watcher 140, the secondary watcher 140 returns its verification results to the primary watcher 116 and the primary watcher 116 reports the result as described above in one embodiment. In another embodiment, a signed report of the results from the secondary watcher 140 is produced using a platform based cryptographic hardware component (a Trusted Platform Module (TPM)).

In one embodiment, external server(s) (management console(s)) use the results of the integrity check. For example, the results written to the register(s) 150 may be exported by the chipset to management console(s), which may manage multiple servers. As another example, a signed report (signed using a TPM component) is exported to the management console(s). These management consoles may take action upon a determination that integrity was compromised. For example, they may cause the machine to shut down. As another example, they may cause a notification (e.g., email, text message, etc.) to be automatically generated and sent to an administrator and/or a phone call to be automatically placed to an administrator. The management consoles may generate forensic cookies or other log files that can later be used and analyzed by enforcement agencies.

Flow moves from operation 325 to operation 330, where the watcher 116 exits. For example, the watcher 116 issues a trigger to exit the watcher mode (e.g., a VMRESUME instruction), which will cause the VMM 118 to resume its execution. Flow then moves to operation 335 where the VMM 118 resumes its execution.

In another embodiment, the CPU hardware 120 may provide a secure pathway through other microcontroller(s) that are embedded inside the processor and/or chipset in order to export the report to a management entity (in addition to or in lieu of using the set of hardware register(s) 130 for reporting). Such a management entity may include, for example, a system management application or a cloud management application.

Thus, embodiments described herein describe the ability to check VMM integrity after the initial VMM has been loaded through a processor hardware driven run-time VMM integrity monitor (the watcher). As previously described, the check may be performed periodically and/or upon certain event(s) occurring, thereby providing ongoing assurance of VMM integrity. In addition, embodiments provide for a protected execution space for the run-time integrity checker described herein. Thus, the run-time integrity of VMM can be protected thereby resolving a security concern that exists today for deployment of virtualized servers in the cloud environment.

Exemplary Core Architectures, Processors, and Computer Architectures

Processor cores may be implemented in different ways, for different purposes, and in different processors. For instance, implementations of such cores may include: 1) a general purpose in-order core intended for general-purpose computing; 2) a high performance general purpose out-of-order core intended for general-purpose computing; 3) a special purpose core intended primarily for graphics and/or scientific (throughput) computing. Implementations of different processors may include: 1) a CPU including one or more general purpose in-order cores intended for general-purpose computing and/or one or more general purpose out-of-order cores intended for general-purpose computing; and 2) a coprocessor including one or more special purpose cores intended primarily for graphics and/or scientific (throughput). Such different processors lead to different computer system architectures, which may include: 1) the coprocessor on a separate chip from the CPU; 2) the coprocessor on a separate die in the same package as a CPU; 3) the coprocessor on the same die as a CPU (in which case, such a coprocessor is sometimes referred to as special purpose logic, such as integrated graphics and/or scientific (throughput) logic, or as special purpose cores); and 4) a system on a chip that may include on the same die the described CPU (sometimes referred to as the application core(s) or application processor(s)), the above described coprocessor, and additional functionality. Exemplary core architectures are described next, followed by descriptions of exemplary processors and computer architectures.

Exemplary Core Architectures

In-Order and Out-of-Order Core Block Diagram

FIG. 4A is a block diagram illustrating both an exemplary in-order pipeline and an exemplary register renaming, out-of-order issue/execution pipeline according to embodiments of the invention. FIG. 4B is a block diagram illustrating both an exemplary embodiment of an in-order architecture core and an exemplary register renaming, out-of-order issue/execution architecture core to be included in a processor according to embodiments of the invention. The solid lined boxes in FIGS. 4A-B illustrate the in-order pipeline and in-order core, while the optional addition of the dashed lined boxes illustrates the register renaming, out-of-order issue/execution pipeline and core. Given that the in-order aspect is a subset of the out-of-order aspect, the out-of-order aspect will be described.

In FIG. 4A, a processor pipeline 400 includes a fetch stage 402, a length decode stage 404, a decode stage 406, an allocation stage 408, a renaming stage 410, a scheduling (also known as a dispatch or issue) stage 412, a register read/memory read stage 414, an execute stage 416, a write back/memory write stage 418, an exception handling stage 422, and a commit stage 424.

FIG. 4B shows processor core 490 including a front end unit 430 coupled to an execution engine unit 450, and both are coupled to a memory unit 470. The core 490 may be a reduced instruction set computing (RISC) core, a complex instruction set computing (CISC) core, a very long instruction word (VLIW) core, or a hybrid or alternative core type. As yet another option, the core 490 may be a special-purpose core, such as, for example, a network or communication core, compression engine, coprocessor core, general purpose computing graphics processing unit (GPGPU) core, graphics core, or the like.

The front end unit 430 includes a branch prediction unit 432 coupled to an instruction cache unit 434, which is coupled to an instruction translation lookaside buffer (TLB) 436, which is coupled to an instruction fetch unit 438, which is coupled to a decode unit 440. The decode unit 440 (or decoder) may decode instructions, and generate as an output one or more micro-operations, micro-code entry points, microinstructions, other instructions, or other control signals, which are decoded from, or which otherwise reflect, or are derived from, the original instructions. The decode unit 440 may be implemented using various different mechanisms. Examples of suitable mechanisms include, but are not limited to, look-up tables, hardware implementations, programmable logic arrays (PLAs), microcode read only memories (ROMs), etc. In one embodiment, the core 490 includes a microcode ROM or other medium that stores microcode for certain macroinstructions (e.g., in decode unit 440 or otherwise within the front end unit 430). The decode unit 440 is coupled to a rename/allocator unit 452 in the execution engine unit 450.

The execution engine unit 450 includes the rename/allocator unit 452 coupled to a retirement unit 454 and a set of one or more scheduler unit(s) 456. The scheduler unit(s) 456 represents any number of different schedulers, including reservations stations, central instruction window, etc. The scheduler unit(s) 456 is coupled to the physical register file(s) unit(s) 458. Each of the physical register file(s) units 458 represents one or more physical register files, different ones of which store one or more different data types, such as scalar integer, scalar floating point, packed integer, packed floating point, vector integer, vector floating point, status (e.g., an instruction pointer that is the address of the next instruction to be executed), etc. In one embodiment, the physical register file(s) unit 458 comprises a vector registers unit, a write mask registers unit, and a scalar registers unit. These register units may provide architectural vector registers, vector mask registers, and general purpose registers. The physical register file(s) unit(s) 458 is overlapped by the retirement unit 454 to illustrate various ways in which register renaming and out-of-order execution may be implemented (e.g., using a reorder buffer(s) and a retirement register file(s); using a future file(s), a history buffer(s), and a retirement register file(s); using a register maps and a pool of registers; etc.). The retirement unit 454 and the physical register file(s) unit(s) 458 are coupled to the execution cluster(s) 460. The execution cluster(s) 460 includes a set of one or more execution units 462 and a set of one or more memory access units 464. The execution units 462 may perform various operations (e.g., shifts, addition, subtraction, multiplication) and on various types of data (e.g., scalar floating point, packed integer, packed floating point, vector integer, vector floating point). While some embodiments may include a number of execution units dedicated to specific functions or sets of functions, other embodiments may include only one execution unit or multiple execution units that all perform all functions. The scheduler unit(s) 456, physical register file(s) unit(s) 458, and execution cluster(s) 460 are shown as being possibly plural because certain embodiments create separate pipelines for certain types of data/operations (e.g., a scalar integer pipeline, a scalar floating point/packed integer/packed floating point/vector integer/vector floating point pipeline, and/or a memory access pipeline that each have their own scheduler unit, physical register file(s) unit, and/or execution cluster—and in the case of a separate memory access pipeline, certain embodiments are implemented in which only the execution cluster of this pipeline has the memory access unit(s) 464). It should also be understood that where separate pipelines are used, one or more of these pipelines may be out-of-order issue/execution and the rest in-order.

The set of memory access units 464 is coupled to the memory unit 470, which includes a data TLB unit 472 coupled to a data cache unit 474 coupled to a level 2 (L2) cache unit 476. In one exemplary embodiment, the memory access units 464 may include a load unit, a store address unit, and a store data unit, each of which is coupled to the data TLB unit 472 in the memory unit 470. The instruction cache unit 434 is further coupled to a level 2 (L2) cache unit 476 in the memory unit 470. The L2 cache unit 476 is coupled to one or more other levels of cache and eventually to a main memory.

By way of example, the exemplary register renaming, out-of-order issue/execution core architecture may implement the pipeline 400 as follows: 1) the instruction fetch 438 performs the fetch and length decoding stages 402 and 404; 2) the decode unit 440 performs the decode stage 406; 3) the rename/allocator unit 452 performs the allocation stage 408 and renaming stage 410; 4) the scheduler unit(s) 456 performs the schedule stage 412; 5) the physical register file(s) unit(s) 458 and the memory unit 470 perform the register read/memory read stage 414; the execution cluster 460 perform the execute stage 416; 6) the memory unit 470 and the physical register file(s) unit(s) 458 perform the write back/memory write stage 418; 7) various units may be involved in the exception handling stage 422; and 8) the retirement unit 454 and the physical register file(s) unit(s) 458 perform the commit stage 424.

The core 490 may support one or more instructions sets (e.g., the x86 instruction set (with some extensions that have been added with newer versions); the MIPS instruction set of MIPS Technologies of Sunnyvale, Calif.; the ARM instruction set (with optional additional extensions such as NEON) of ARM Holdings of Sunnyvale, Calif.), including the instruction(s) described herein. In one embodiment, the core 490 includes logic to support a packed data instruction set extension (e.g., AVX1, AVX2), thereby allowing the operations used by many multimedia applications to be performed using packed data.

It should be understood that the core may support multi-threading (executing two or more parallel sets of operations or threads), and may do so in a variety of ways including time sliced multithreading, simultaneous multithreading (where a single physical core provides a logical core for each of the threads that physical core is simultaneously multi-threading), or a combination thereof (e.g., time sliced fetching and decoding and simultaneous multithreading thereafter such as in the Intel® Hyperthreading technology).

While register renaming is described in the context of out-of-order execution, it should be understood that register renaming may be used in an in-order architecture. While the illustrated embodiment of the processor also includes separate instruction and data cache units 434/474 and a shared L2 cache unit 476, alternative embodiments may have a single internal cache for both instructions and data, such as, for example, a Level 1 (L1) internal cache, or multiple levels of internal cache. In some embodiments, the system may include a combination of an internal cache and an external cache that is external to the core and/or the processor. Alternatively, all of the cache may be external to the core and/or the processor.

Specific Exemplary In-Order Core Architecture

FIGS. 5A-B illustrate a block diagram of a more specific exemplary in-order core architecture, which core would be one of several logic blocks (including other cores of the same type and/or different types) in a chip. The logic blocks communicate through a high-bandwidth interconnect network (e.g., a ring network) with some fixed function logic, memory I/O interfaces, and other necessary I/O logic, depending on the application.

FIG. 5A is a block diagram of a single processor core, along with its connection to the on-die interconnect network 502 and with its local subset of the Level 2 (L2) cache 504, according to embodiments of the invention. In one embodiment, an instruction decoder 500 supports the x86 instruction set with a packed data instruction set extension. An L1 cache 506 allows low-latency accesses to cache memory into the scalar and vector units. While in one embodiment (to simplify the design), a scalar unit 508 and a vector unit 510 use separate register sets (respectively, scalar registers 512 and vector registers 514) and data transferred between them is written to memory and then read back in from a level 1 (L1) cache 506, alternative embodiments of the invention may use a different approach (e.g., use a single register set or include a communication path that allow data to be transferred between the two register files without being written and read back).

The local subset of the L2 cache 504 is part of a global L2 cache that is divided into separate local subsets, one per processor core. Each processor core has a direct access path to its own local subset of the L2 cache 504. Data read by a processor core is stored in its L2 cache subset 504 and can be accessed quickly, in parallel with other processor cores accessing their own local L2 cache subsets. Data written by a processor core is stored in its own L2 cache subset 504 and is flushed from other subsets, if necessary. The ring network ensures coherency for shared data. The ring network is bi-directional to allow agents such as processor cores, L2 caches and other logic blocks to communicate with each other within the chip. Each ring data-path is 1012-bits wide per direction.

FIG. 5B is an expanded view of part of the processor core in FIG. 5A according to embodiments of the invention. FIG. 5B includes an L1 data cache 506A part of the L1 cache 504, as well as more detail regarding the vector unit 510 and the vector registers 514. Specifically, the vector unit 510 is a 16-wide vector processing unit (VPU) (see the 16-wide ALU 528), which executes one or more of integer, single-precision float, and double-precision float instructions. The VPU supports swizzling the register inputs with swizzle unit 520, numeric conversion with numeric convert units 522A-B, and replication with replication unit 524 on the memory input. Write mask registers 526 allow predicating resulting vector writes.

Processor with Integrated Memory Controller and Graphics

Figure 6:
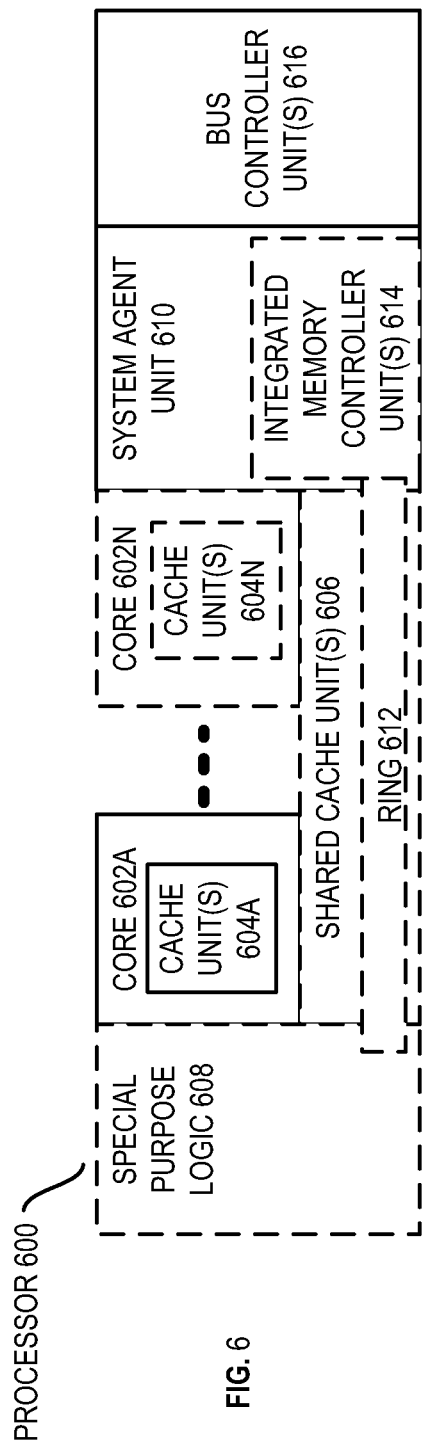
FIG. 6 is a block diagram of a processor that may have more than one core, may have an integrated memory controller, and may have integrated graphics according to embodiments of the invention.

FIG. 6 is a block diagram of a processor 600 that may have more than one core, may have an integrated memory controller, and may have integrated graphics according to embodiments of the invention. The solid lined boxes in FIG. 6 illustrate a processor 600 with a single core 602A, a system agent 610, a set of one or more bus controller units 616, while the optional addition of the dashed lined boxes illustrates an alternative processor 600 with multiple cores 602A-N, a set of one or more integrated memory controller unit(s) 614 in the system agent unit 610, and special purpose logic 608.

Thus, different implementations of the processor 600 may include: 1) a CPU with the special purpose logic 608 being integrated graphics and/or scientific (throughput) logic (which may include one or more cores), and the cores 602A-N being one or more general purpose cores (e.g., general purpose in-order cores, general purpose out-of-order cores, a combination of the two); 2) a coprocessor with the cores 602A-N being a large number of special purpose cores intended primarily for graphics and/or scientific (throughput); and 3) a coprocessor with the cores 602A-N being a large number of general purpose in-order cores. Thus, the processor 600 may be a general-purpose processor, coprocessor or special-purpose processor, such as, for example, a network or communication processor, compression engine, graphics processor, GPGPU (general purpose graphics processing unit), a high-throughput many integrated core (MIC) coprocessor (including 30 or more cores), embedded processor, or the like. The processor may be implemented on one or more chips. The processor 600 may be a part of and/or may be implemented on one or more substrates using any of a number of process technologies, such as, for example, BiCMOS, CMOS, or NMOS.

The memory hierarchy includes one or more levels of cache within the cores, a set or one or more shared cache units 606, and external memory (not shown) coupled to the set of integrated memory controller units 614. The set of shared cache units 606 may include one or more mid-level caches, such as level 2 (L2), level 3 (L3), level 4 (L4), or other levels of cache, a last level cache (LLC), and/or combinations thereof. While in one embodiment a ring based interconnect unit 612 interconnects the integrated graphics logic 608, the set of shared cache units 606, and the system agent unit 610/integrated memory controller unit(s) 614, alternative embodiments may use any number of well-known techniques for interconnecting such units. In one embodiment, coherency is maintained between one or more cache units 606 and cores 602-A-N.

In some embodiments, one or more of the cores 602A-N are capable of multi-threading. The system agent 610 includes those components coordinating and operating cores 602A-N. The system agent unit 610 may include for example a power control unit (PCU) and a display unit. The PCU may be or include logic and components needed for regulating the power state of the cores 602A-N and the integrated graphics logic 608. The display unit is for driving one or more externally connected displays.

The cores 602A-N may be homogenous or heterogeneous in terms of architecture instruction set; that is, two or more of the cores 602A-N may be capable of execution the same instruction set, while others may be capable of executing only a subset of that instruction set or a different instruction set.

Exemplary Computer Architectures

FIGS. 7-10 are block diagrams of exemplary computer architectures. Other system designs and configurations known in the arts for laptops, desktops, handheld PCs, personal digital assistants, engineering workstations, servers, network devices, network hubs, switches, embedded processors, digital signal processors (DSPs), graphics devices, video game devices, set-top boxes, micro controllers, cell phones, portable media players, hand held devices, and various other electronic devices, are also suitable. In general, a huge variety of systems or electronic devices capable of incorporating a processor and/or other execution logic as disclosed herein are generally suitable.

Figure 7:
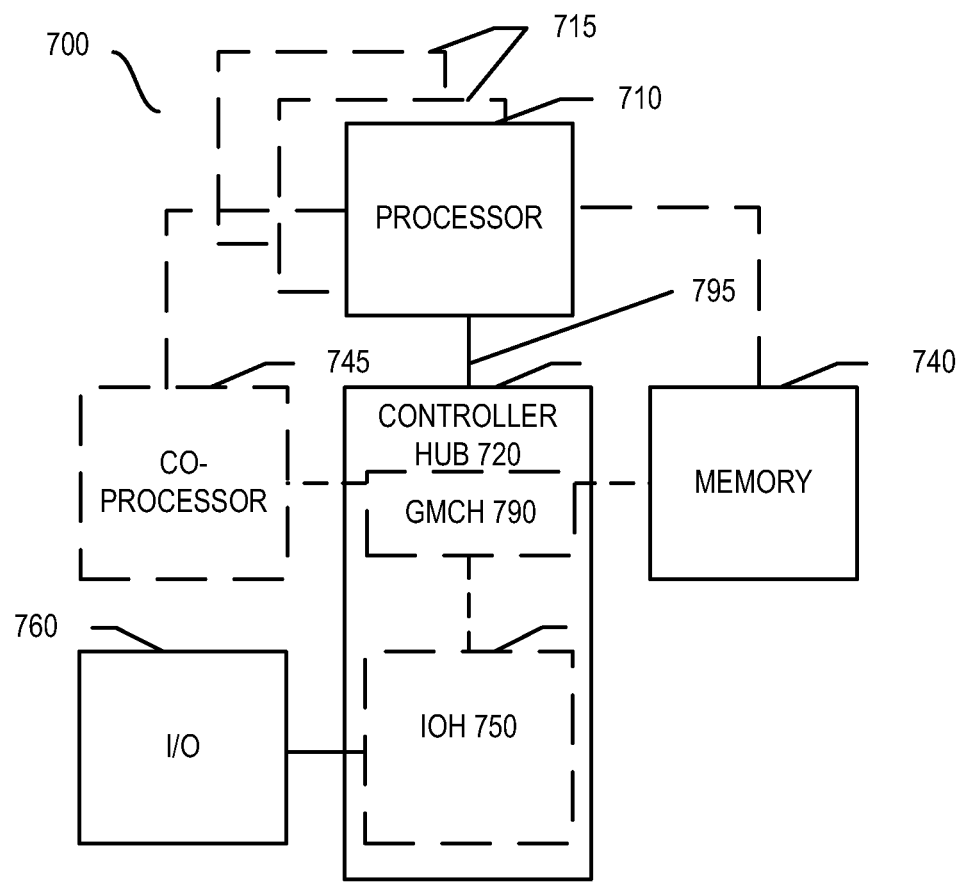
FIG. 7 is a block diagram of a system in accordance with one embodiment of the present invention.

Referring now to FIG. 7, shown is a block diagram of a system 700 in accordance with one embodiment of the present invention. The system 700 may include one or more processors 710, 715, which are coupled to a controller hub 720. In one embodiment the controller hub 720 includes a graphics memory controller hub (GMCH) 790 and an Input/Output Hub (IOH) 750 (which may be on separate chips); the GMCH 790 includes memory and graphics controllers to which are coupled memory 740 and a coprocessor 745; the IOH 750 is couples input/output (I/O) devices 760 to the GMCH 790. Alternatively, one or both of the memory and graphics controllers are integrated within the processor (as described herein), the memory 740 and the coprocessor 745 are coupled directly to the processor 710, and the controller hub 720 in a single chip with the IOH 750.

The optional nature of additional processors 715 is denoted in FIG. 7 with broken lines. Each processor 710, 715 may include one or more of the processing cores described herein and may be some version of the processor 600.

The memory 740 may be, for example, dynamic random access memory (DRAM), phase change memory (PCM), or a combination of the two. For at least one embodiment, the controller hub 720 communicates with the processor(s) 710, 715 via a multi-drop bus, such as a frontside bus (FSB), point-to-point interface such as QuickPath Interconnect (QPI), or similar connection 795.

In one embodiment, the coprocessor 745 is a special-purpose processor, such as, for example, a high-throughput MIC processor, a network or communication processor, compression engine, graphics processor, GPGPU, embedded processor, or the like. In one embodiment, controller hub 720 may include an integrated graphics accelerator.

There can be a variety of differences between the physical resources 710, 715 in terms of a spectrum of metrics of merit including architectural, microarchitectural, thermal, power consumption characteristics, and the like.

In one embodiment, the processor 710 executes instructions that control data processing operations of a general type. Embedded within the instructions may be coprocessor instructions. The processor 710 recognizes these coprocessor instructions as being of a type that should be executed by the attached coprocessor 745. Accordingly, the processor 710 issues these coprocessor instructions (or control signals representing coprocessor instructions) on a coprocessor bus or other interconnect, to coprocessor 745. Coprocessor(s) 745 accept and execute the received coprocessor instructions.

Figure 8:
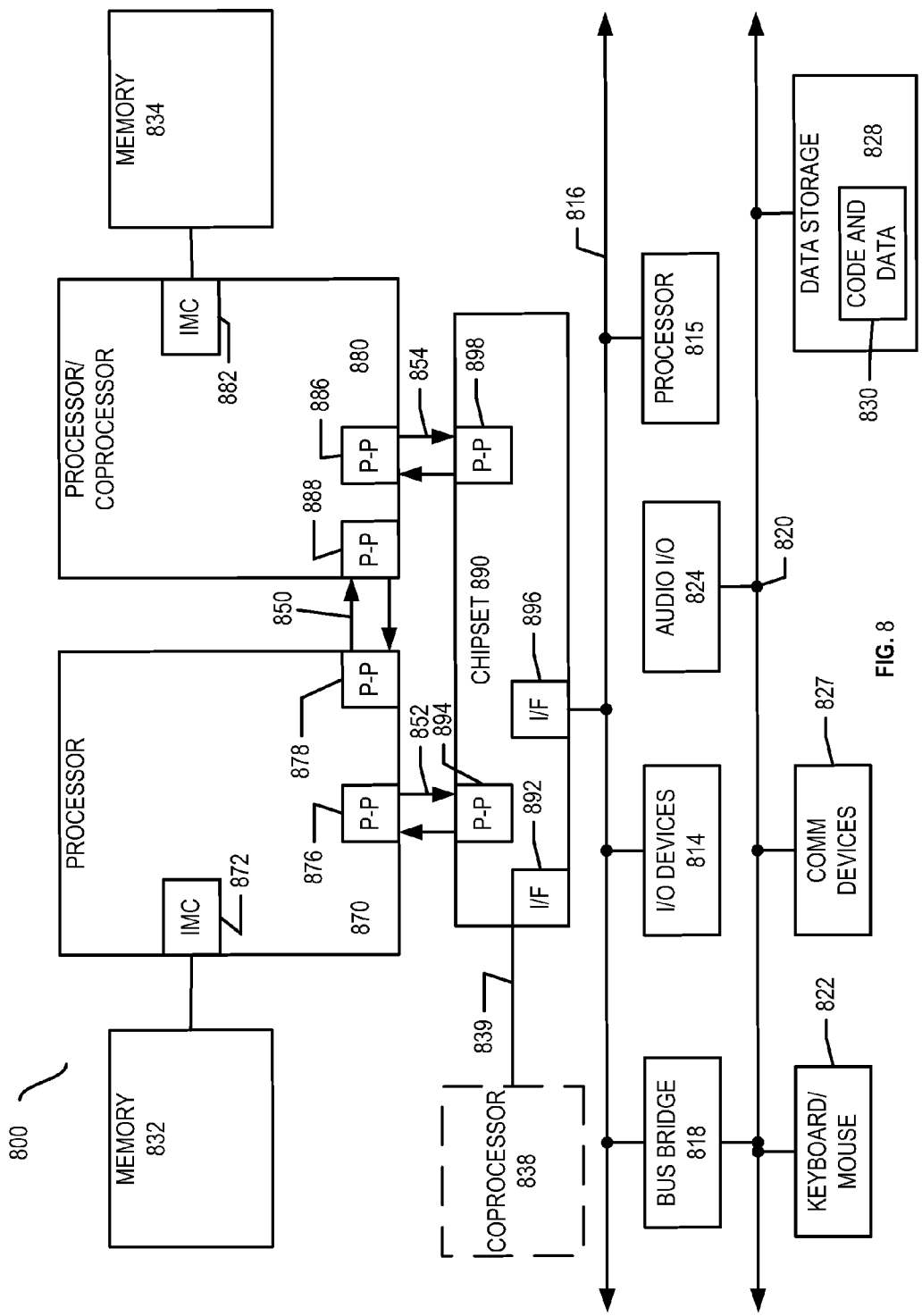
FIG. 8 is a block diagram of a first more specific exemplary system in accordance with an embodiment of the present invention.

Referring now to FIG. 8, shown is a block diagram of a first more specific exemplary system 800 in accordance with an embodiment of the present invention. As shown in FIG. 8, multiprocessor system 800 is a point-to-point interconnect system, and includes a first processor 870 and a second processor 880 coupled via a point-to-point interconnect 850. Each of processors 870 and 880 may be some version of the processor 600. In one embodiment of the invention, processors 870 and 880 are respectively processors 710 and 715, while coprocessor 838 is coprocessor 745. In another embodiment, processors 870 and 880 are respectively processor 710 coprocessor 745.

Processors 870 and 880 are shown including integrated memory controller (IMC) units 872 and 882, respectively. Processor 870 also includes as part of its bus controller units point-to-point (P-P) interfaces 876 and 878; similarly, second processor 880 includes P-P interfaces 886 and 888. Processors 870, 880 may exchange information via a point-to-point (P-P) interface 850 using P-P interface circuits 878, 888. As shown in FIG. 8, IMCs 872 and 882 couple the processors to respective memories, namely a memory 832 and a memory 834, which may be portions of main memory locally attached to the respective processors.

Processors 870, 880 may each exchange information with a chipset 890 via individual P-P interfaces 852, 854 using point to point interface circuits 876, 894, 886, 898. Chipset 890 may optionally exchange information with the coprocessor 838 via a high-performance interface 839. In one embodiment, the coprocessor 838 is a special-purpose processor, such as, for example, a high-throughput MIC processor, a network or communication processor, compression engine, graphics processor, GPGPU, embedded processor, or the like.

A shared cache (not shown) may be included in either processor or outside of both processors, yet connected with the processors via P-P interconnect, such that either or both processors' local cache information may be stored in the shared cache if a processor is placed into a low power mode.

Chipset 890 may be coupled to a first bus 816 via an interface 896. In one embodiment, first bus 816 may be a Peripheral Component Interconnect (PCI) bus, or a bus such as a PCI Express bus or another third generation I/O interconnect bus, although the scope of the present invention is not so limited.

As shown in FIG. 8, various I/O devices 814 may be coupled to first bus 816, along with a bus bridge 818 which couples first bus 816 to a second bus 820. In one embodiment, one or more additional processor(s) 815, such as coprocessors, high-throughput MIC processors, GPGPU's, accelerators (such as, e.g., graphics accelerators or digital signal processing (DSP) units), field programmable gate arrays, or any other processor, are coupled to first bus 816. In one embodiment, second bus 820 may be a low pin count (LPC) bus. Various devices may be coupled to a second bus 820 including, for example, a keyboard and/or mouse 822, communication devices 827 and a storage unit 828 such as a disk drive or other mass storage device which may include instructions/code and data 830, in one embodiment. Further, an audio I/O 824 may be coupled to the second bus 820. Note that other architectures are possible. For example, instead of the point-to-point architecture of FIG. 8, a system may implement a multi-drop bus or other such architecture.

Figure 9:
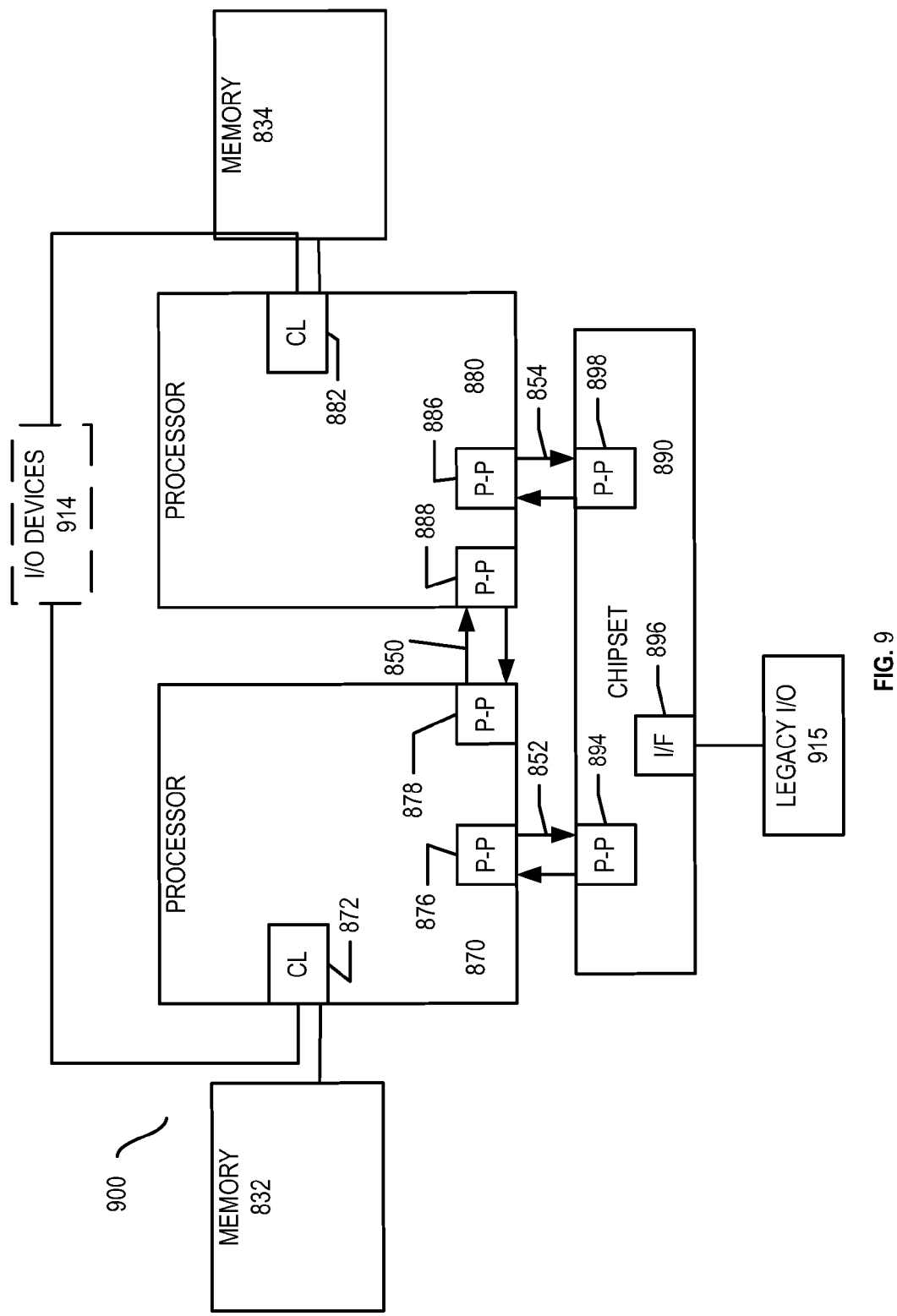
FIG. 9 is a block diagram of a second more specific exemplary system in accordance with an embodiment of the present invention.

Referring now to FIG. 9, shown is a block diagram of a second more specific exemplary system 900 in accordance with an embodiment of the present invention. Like elements in FIGS. 8 and 9 bear like reference numerals, and certain aspects of FIG. 8 have been omitted from FIG. 9 in order to avoid obscuring other aspects of FIG. 9.

FIG. 9 illustrates that the processors 870, 880 may include integrated memory and I/O control logic ("CL") 872 and 882, respectively. Thus, the CL 872, 882 include integrated memory controller units and include I/O control logic. FIG. 9 illustrates that not only are the memories 832, 834 coupled to the CL 872, 882, but also that I/O devices 914 are also coupled to the control logic 872, 882. Legacy I/O devices 915 are coupled to the chipset 890.

Figure 10:
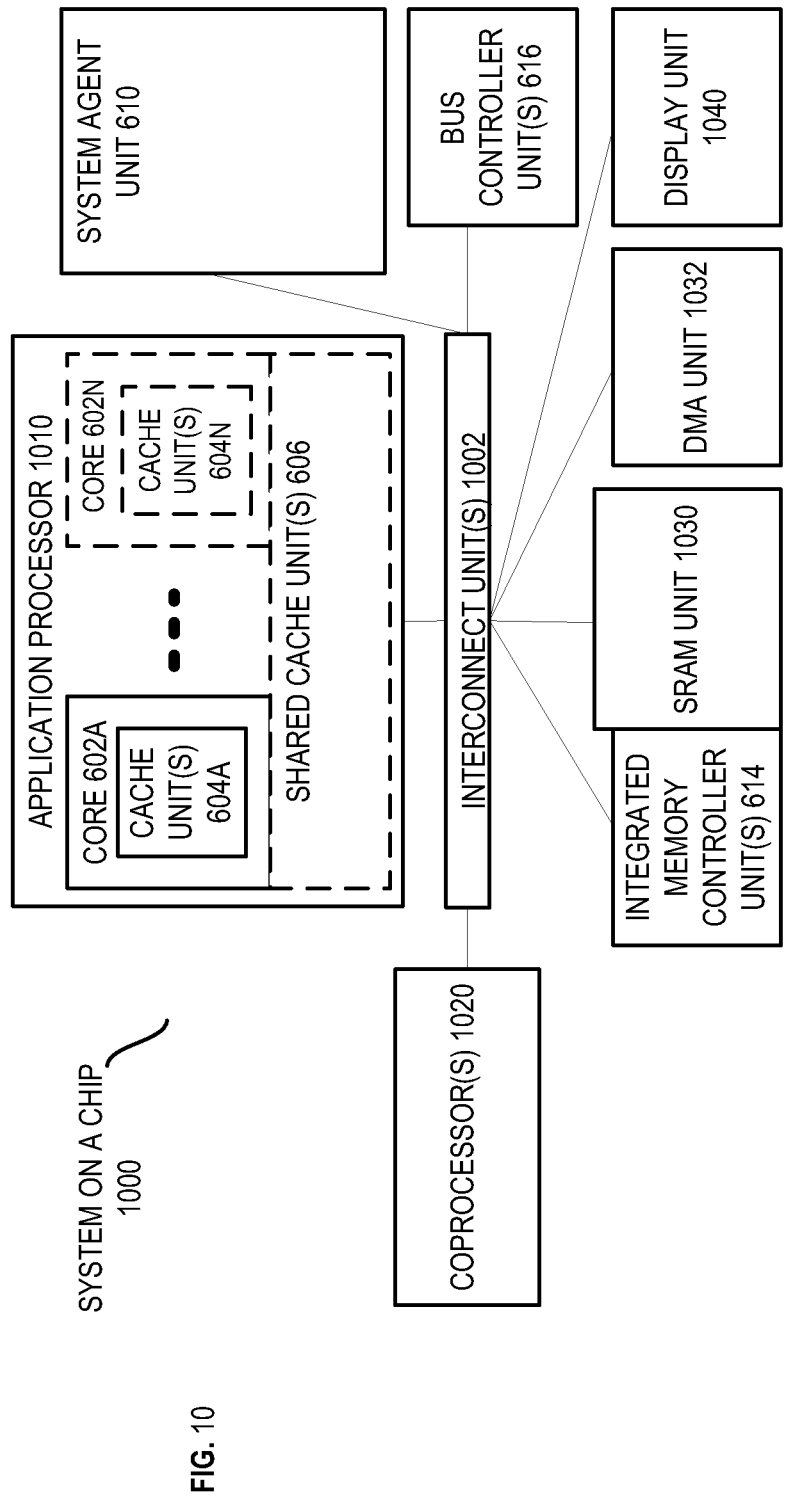
FIG. 10 is a block diagram of a SoC in accordance with an embodiment of the present invention.

Referring now to FIG. 10, shown is a block diagram of a SoC 1000 in accordance with an embodiment of the present invention. Similar elements in FIG. 6 bear like reference numerals. Also, dashed lined boxes are optional features on more advanced SoCs. In FIG. 10, an interconnect unit(s) 1002 is coupled to: an application processor 1010 which includes a set of one or more cores 202A-N and shared cache unit(s) 606; a system agent unit 610; a bus controller unit(s) 616; an integrated memory controller unit(s) 614; a set or one or more coprocessors 1020 which may include integrated graphics logic, an image processor, an audio processor, and a video processor; an static random access memory (SRAM) unit 1030; a direct memory access (DMA) unit 1032; and a display unit 1040 for coupling to one or more external displays. In one embodiment, the coprocessor(s) 1020 include a special-purpose processor, such as, for example, a network or communication processor, compression engine, GPGPU, a high-throughput MIC processor, embedded processor, or the like.

Embodiments of the mechanisms disclosed herein may be implemented in hardware, software, firmware, or a combination of such implementation approaches. Embodiments of the invention may be implemented as computer programs or program code executing on programmable systems comprising at least one processor, a storage system (including volatile and non-volatile memory and/or storage elements), at least one input device, and at least one output device.

Program code, such as code 830 illustrated in FIG. 8, may be applied to input instructions to perform the functions described herein and generate output information. The output information may be applied to one or more output devices, in known fashion. For purposes of this application, a processing system includes any system that has a processor, such as, for example; a digital signal processor (DSP), a microcontroller, an application specific integrated circuit (ASIC), or a microprocessor.

The program code may be implemented in a high level procedural or object oriented programming language to communicate with a processing system. The program code may also be implemented in assembly or machine language, if desired. In fact, the mechanisms described herein are not limited in scope to any particular programming language. In any case, the language may be a compiled or interpreted language.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor.

Such machine-readable storage media may include, without limitation, non-transitory, tangible arrangements of articles manufactured or formed by a machine or device, including storage media such as hard disks, any other type of disk including floppy disks, optical disks, compact disk read-only memories (CD-ROMs), compact disk rewritable's (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), phase change memory (PCM), magnetic or optical cards, or any other type of media suitable for storing electronic instructions.

Accordingly, embodiments of the invention also include non-transitory, tangible machine-readable media containing instructions or containing design data, such as Hardware Description Language (HDL), which defines structures, circuits, apparatuses, processors and/or system features described herein. Such embodiments may also be referred to as program products.

While the flow diagrams in the figures show a particular order of operations performed by certain embodiments of the invention, it should be understood that such order is exemplary (e.g., alternative embodiments may perform the operations in a different order, combine certain operations, overlap certain operations, etc.).

In the description above, for the purposes of explanation, numerous specific details have been set forth in order to provide a thorough understanding of the embodiments of the invention. It will be apparent however, to one skilled in the art, that one or more other embodiments may be practiced without some of these specific details. The particular embodiments described are not provided to limit the invention but to illustrate embodiments of the invention. The scope of the invention is not to be determined by the specific examples provided above but only by the claims below.

What is claimed is:

1. An apparatus, comprising:
a set of one or more hardware range registers to protect a contiguous memory space that is to store a virtual machine monitor (VMM) runtime integrity watcher, wherein the set of hardware range registers are to protect the VMM runtime integrity watcher from being modified when loaded into the contiguous memory space; and
the VMM runtime integrity watcher, when executed, is to perform an integrity check on a VMM during runtime of the VMM.

2. The apparatus of claim 1, further comprising:
a hardware timer to generate an event to invoke execution of the VMM runtime integrity watcher during runtime of the VMM.

3. The apparatus of claim 2, wherein execution of the VMM is preempted upon the event being generated.

4. The apparatus of claim 1, wherein the VMM runtime integrity watcher is further to, when executed, report results of the integrity check.

5. The apparatus of claim 4, wherein the VMM runtime integrity watcher is to report results of the integrity check to one of a system management application and a cloud management application.

6. The apparatus of claim 4, further comprising:
a set of one or more hardware reporting registers; and
wherein the VMM runtime integrity watcher is to write to the set of hardware reporting registers to indicate whether the VMM has been compromised.

7. The apparatus of claim 6, wherein the set of hardware reporting registers are writable only by the VMM runtime integrity watcher and readable by any entity.

8. The apparatus of claim 7, wherein the apparatus comprises a multiprocessor system to incorporate the set of one or more hardware range registers, the VMM runtime integrity watcher, and the set of one or more hardware reporting registers.

9. The apparatus of claim 7, wherein the apparatus comprises a microprocessor to incorporate the set of one or more hardware range registers, the VMM runtime integrity watcher, and the set of one or more hardware reporting registers.

10. The apparatus of claim 7, wherein the apparatus comprises a digital signal processor to incorporate the set of one or more hardware range registers, the VMM runtime integrity watcher, and the set of one or more hardware reporting registers.

11. The apparatus of claim 7, wherein the apparatus comprises an application specific integrated circuit to incorporate the set of one or more hardware range registers, the VMM runtime integrity watcher, and the set of one or more hardware reporting registers.

12. The apparatus of claim 7, wherein the apparatus comprises a System on a Chip to incorporate the set of one or more hardware range registers, the VMM runtime integrity watcher, and the set of one or more hardware reporting registers.

13. A computer-implemented method in a computing system, comprising:
loading a virtual machine monitor (VMM) runtime integrity watcher into a contiguous memory space of the computing system, wherein the contiguous memory space is in a location defined by a set of one or more hardware range registers that indicate that the contiguous memory space holding the loaded VMM runtime integrity watcher is not to be-modified;
detecting an event to invoke execution of the VMM runtime integrity watcher;
responsive to the detected event, executing the VMM runtime integrity watcher; and
performing, by the VMM runtime integrity watcher, an integrity check on a VMM during runtime of the VMM.

14. The computer-implemented method of claim 13, wherein event is generated by a hardware timer that is configured to periodically generate events.

15. The computer-implemented method of claim 13, wherein responsive to the detected event, preempting execution of the VMM.

16. The computer-implemented method of claim 13, further comprising:
reporting, by the VMM runtime integrity watcher, a result of the integrity check.

17. The computer-implemented method of claim 16, wherein reporting includes writing the result of the integrity check to a set of one or more hardware reporting registers.

18. The computer-implemented method of claim 16, wherein reporting includes reporting the result of the integrity check to one of a system management application and a cloud management application.

\* \* \* \* \*